(12) United States Patent
Brekke et al.

(10) Patent No.: US 7,326,421 B2
(45) Date of Patent: Feb. 5, 2008

(54) DEVICE AND METHODS FOR SEQUENTIAL, REGIONAL DELIVERY OF MULTIPLE CYTOTOXIC AGENTS AND DIRECTED ASSEMBLY OF WOUND REPAIR TISSUES

(75) Inventors: John H. Brekke, Duluth, MN (US); John H. Gubbe, Duluth, MN (US)

(73) Assignee: Kensey Nash Corporation, Exton, PA (US)

( * ) Notice: Subject to any disclaimer, the term of this patent is extended or adjusted under 35 U.S.C. 154(b) by 749 days.

(21) Appl. No.: 10/690,972

(22) Filed: Oct. 21, 2003

(65) Prior Publication Data

US 2004/0126426 A1    Jul. 1, 2004

(51) Int. Cl.
*A61F 2/00* (2006.01)
*A61K 31/33* (2006.01)
*A61K 31/335* (2006.01)
*A61K 31/28* (2006.01)

(52) U.S. Cl. ............... 424/426; 514/183; 514/449; 514/492

(58) Field of Classification Search .............. None
See application file for complete search history.

(56) References Cited

U.S. PATENT DOCUMENTS

| | | | |
|---|---|---|---|
| 4,186,448 A | 2/1980 | Brekke | 3/1.9 |
| 4,942,184 A | 7/1990 | Haugwitz et al. | 514/449 |
| 5,133,755 A | 7/1992 | Brekke | 623/16 |
| 5,505,957 A | 4/1996 | D'Angelo et al. | 424/449 |
| 5,616,568 A | 4/1997 | Pouyani et al. | 514/54 |
| 5,855,608 A | 1/1999 | Brekke et al. | 623/11 |
| 5,977,163 A | 11/1999 | Li et al. | 514/449 |
| 5,981,825 A | 11/1999 | Brekke | 623/11 |
| 6,262,107 B1 | 7/2001 | Li et al. | 514/449 |
| 6,264,701 B1 | 7/2001 | Brekke | 623/23.72 |
| 6,902,743 B1 * | 6/2005 | Setterstrom et al. | 424/489 |
| 2002/0032488 A1 | 3/2002 | Brekke et al. | 623/23.72 |
| 2002/0055666 A1 * | 5/2002 | Hunter et al. | 600/1 |

FOREIGN PATENT DOCUMENTS

WO    WO 99/02151    1/1999

OTHER PUBLICATIONS

Cecil Textbook of Medicine, 21st Edition, vol. 1, Goldman et al., (Eds), published 2000 by W.B.Saunders, (PA), pp. 1060-1074.*

Tara Pouyani and Glenn D. Prestwich, "Functionalized Derivatives of Hyaluronic Acid Oligosaccharides: Drug Carriers and Novel Biomaterials", *Bioconjugate Chem.* 1994, 5, pp. 339-347.

John K. Jackson, Kevin C. Skinner, Laurette Burgess, Tyler Sun, William L. Hunter and Helen M. Burt, "Paclitaxel-Loaded Crosslinked Hyaluronic Acid Films for the Prevention of Postsurgical Adhesions", *Pharmaceutical Research*, vol. 19, No. 4, Apr. 2002, pp. 411-417.

Ogura, Haruo, S. Nagai and K. Takeda: "A Novel Reagent (N-Succinimidyl Diphenylphosphate) for Synthesis of Active Ester and Peptide", *Tetrahedron Letters*, vol. 21, pp. 1467-1468, date unavailable.

Pouyani, Tara, J. W. Kuo, G. S. Harbinson and G. D. Prestwich: "Solid-State NMR of N-Acylureas Derived from the Reaction of Hyaluronic Acid with Isotopically-Labeled Carbodiimides", *J. AM. Chem. Soc.*, 1992, 114, pp. 5972-5976.

Pouyani, Tara and G. D. Prestwich: "Biotinylated Hyaluronic Acid: A New Tool for Probing Hyaluronate-Receptor Interactions", *Bioconjugate Chem.*, 1994, 5, pp. 370-372.

Pouyani, Tara, G. S. Harbinson and G. D. Prestwich: "Novel Hydrogels of Hyaluronic Acid: Synthesis, Surface Morphology; and Solid-State NMR", *J. Am. Chem. Soc.*, 1994, 116, pp. 7515-7522.

Dosio, Franco, P. Brusa, P. Crosasso, S. Arpicco and L. Cattel: "Preparation, Characterization and Properties In Vitro and In Vivo of a Paclitaxel-Albumin Conjugate", *Journal of Controlled Release*, 1997, 47, pp. 293-304.

Vercruysse, Koen P., D. M. Marecak, J.F. Marecek and G. D. Prestwich: "Synthesis and in Vitro Degradation of New Polyvalent Hydrazide Cross-Linked Hydrogels of Hyaluronic Acid", *Bioconjugate Chem.*, 1997, 8 pp. 686-694.

Lapcik, Jr., Lubomir and Lubomir Lapcik: "Hyaluronan: Preparation, Structure, Properties, and Applications", *Chemical Reviews*, 1998, 98 (8), pp. 2663-2684.

(Continued)

*Primary Examiner*—Raymond J. Henley, III
(74) *Attorney, Agent, or Firm*—Alan Kamrath; Kamrath & Associates PA

(57) ABSTRACT

An implantable delivery system includes a macrostructure formed of bioresorbable material selected from a group of alphahydroxy acids and defined to include an internal architecture of intercommunicating void spaces. A first cytotoxic agent in the preferred form of cisplatin is joined to the macrostructure during formation. A microstructure in the preferred form of a blend of high molecular weight hyaluronic acid conjugated with a second cytotoxic agent in the preferred form of paclitaxel and of pure high molecular weight hyaluronic acid is invested in the void spaces. Thus, when implanted, the paclitaxel and cisplatin are released sequentially, each initially at high level concentrations followed by lower release. Radiotherapy can be begun after the release of the paclitaxel has been completed but while the cisplatin is being released.

15 Claims, 1 Drawing Sheet

OTHER PUBLICATIONS

Takahasi, Takashi, H. Tsukamoto and H. Yamada: "Design and Synthesis of a Water-Soluble Taxol Analogue: Taxol-Sialyl Conjugate", *Bioorganic & Medicinal Chemistry Letters*, 1998, 8, pp. 113-116.

Luo, Yi and G. D. Prestwich: "Synthesis and Selective Cytotoxicity of a Hyaluronic Acid-Antitumor Bioconjugate", *Bioconjugate Chem.*, 1999, 10, pp. 755-763.

Szycher, M., "Medical/pharmaceutical markets for medical plastics", In Szycher, M., ed, High Performance Biomaterials, Lancaster, PA: Technomic Publishing Company, pp. 3-30, 1991.

Ellis, J.R., "Medical Markets for Radiation Sterilizable Plastics", In Szycher, M., ed, High Performance Biomaterials, Lancaster, PA: Technomic Publishing Company, pp. 31-34, 1991.

Douple, E.B., Richmond, R.C., "Radiosensitization of hypoxic tumor cells by cis- and trans-dichlorodiammineplatinum (II)" *Int. J. Radiat. Oncol. Biol. Phys.*, vol. 5 No. 8: 1369-1372, Aug. 1979.

Twentyman, P.R., Kallman R.F., Brown. J.M., "The effect of time between x-irradiation and chemotherapy on the growth of three solid mouse tumors. III cis-diamminedichloroplatinum" *Int. J. Radial Oncol. Biol. Phys.* vol. 5, No. 8: 1365-1367, Aug. 1979.

Lolich, J.J., "Phase I study of cis-diamminedichloroplatinum (II) administered as a constant 5-day infusion" *Cancer Treat. Rep.*, vol. 64, No. 8-9: 905-908, Aug./Sep. 1980.

Lana S.E., Dernell, W.S., LaRue, S.M., et al., "Slow release cisplatin combined with radiation for the treatment of canine nasal tumors" *Vet. Radiol. Ultrasound*, vol. 38, No. 6: 474-478, 1997.

Brekke, J.H., "A rationale for delivery of osteoinductive proteins" *Tissue Eng.* vol. 2, No. 2: 97-114, 1996.

Zegzula, H.D., Buck, D.C., Brekke, J.H., Wozney, J.M., Hollinger, J.O., "Bone formation with use of rhBMP-2 (recombinant human bone morphogenetic protein-2)" *JBJS* (A), 79-A(12): 1778-1790, 1997.

Brekke, J.H., and Toth, J.M., "Principles of tissue engineering applied to programmable osteogenesis" *J. Biomed Mater. Res.*, 43: 380-397, 1998.

Meadows, C.L., Gher, M.E., Quintero, G., Lafferty, T.A., "A comparison of polylactic acid granules and decalcifled freeze-dried bone allograft in human periodontal osseous defects" *J Periodontal*, vol. 64, No. 2: 103-109, 1993.

Zhang, R., Ma, P.X., "Poly($\alpha$-hydroxyl acids)/hydroxyapatite porous composites for bone-tissue engineering. I. Preparation and morphology" *J. Biomed. Mater. Res.*, 44: 446-455, 1999.

Ma, P.X., Zhang, R., "Microtubular architecture of biodegradable polymer scaffolds" *J. Biomed. Mater. Res.*, 56:469-477, 2001.

Straw, R.C., Withrow, S.J., Cooper, M.F., Powers, B.E., Schwarz, P.D., O'Brien, M.G., Jameson. V.J., Lafferty, M.H., Douple, E.B., Brekke, J.H., "Local slow-release cisplatin therapy after marginal local tumor resection" *Frontiers of Osteosarcoma Research—Interdisciplinary Survey of Clinical and Research Advances*, Eds., Novak, J.F. and McMaster, J.H., Hogrefe & Huber Publishers, 121-123, 1993.

Withrow, S.J., Straw, R.C., Brekke, J.H., Powers, B.E., Cooper, M.F., Ogilvie, G.K., Lafferty, M:, Jameson, V.J., Douple, E.B., Johnson, J.L., Dernell, W.S., "Slow release adjuvant cisplatin for treatment of metastatic canine osteosarcoma" *Eur. J. Exp. Musculoskel. Res.* 4: 105-110, 1995.

Dernell, W.S., Withrow, S.J., Straw, R.C., Powers, B.E., Brekke, J.H., Lafferty, M. "Intracavitary treatment of soft tissue sarcomas in dogs using cisplatin in a biodegradable polymer" *Anticancer Res.* 17: 4499-4506, 1997.

Ehrhart, N., Dernell, W.S., Ehrhart, E.J., Hutchinson, J.M. Douple, E.B., Brekke, J.H., Straw, R.C., Withrow, S.J., "Effects of a controlled-release cisplatin delivery system used after resection of mammary carcinoma in mice" *AJVR*, vol. 60, No. 11, Nov. 1999.

Straw, R.C., Withrow, S.J., Douple, E.B., Brekke, J.H., Cooper, M.F., Schwarz, P.D., Greco, D.S., Powers, B.E., "Effects of cis-diamminedichloroplatinum II released from D,L-polylactic acid implanted adjacent to cortical allografts in dogs" *J. Orthop. Res.* vol. 12: 871-877, 1994.

Frasci, G., Panza, N., Comella, P., Nicolella, G.P., Natale, M., Manzione, L., Bilancia, D., Cioffi, R., Maiorino, L., De Cataldis, G., et al., "Cisplatin, gemcitabine, and paclitaxel in locally advanced or metastatic non-small-cell lung cancer: a phase I-II study" *J. Clin. Oncol.* vol. 17 No. 8: 2316-2325, Aug. 1999.

Aoe, K., Kiura, K., Ueoka, H., Tabata, M., Matsumura, T., Chikamori, M., Matsushita, A., Kohara, H., Harada, M., "Effects of docetaxel with cisplatin or vinorelbine on lung cancer cell lines" *Anticancer Research* 19: 291-300, 1999.

Cancer Facts & Figures-2003. Atlanta Ga: American Cancer Society.

Landis, S.H., Murray, T., Bolden, S., Wingo, P.A., "Cancer Statistics, 1999" *CA—A Cancer Journal for Clinicians* vol. 49, No. 1: 8-31, Jan./Feb. 1999.

Lillehei, K.O., Kong, Q., Withrow, S.J., Kleinschmidt-DeMasters, B., "Efficacy of Intralesionally administered cisplatin-impregnated biodegradable polymer for the treatment of 9L gliosarcoma in the rat" *Neurosurgery*, vol. 39, No. 6: Dec. 1-9, 1996.

Plotkin, D., "The good news and bad news about breast cancer" The Atlantic Monthly, vol. 277, 6: 53-82 (pp. 1-28), 1996.

Fisher, B., Redmond, C., Poisson, R., et al. "Eight-year results of a randomized clinical trial comparing total mastectomy and lumpectomy with or without irradiation in the treatment of breast cancer" *New Engl. J. Med. 30* vol. 320 No. 13: 822-828, Mar. 30, 1989.

Laurent, T.C., Fraser, J.R.E., "Hyaluronan" *FASEB* vol. 6: 2397-2404, Apr. 1992.

Laurent, T.C., Laurent, U.B.G., Fraser, J.R.E., "The structure and function of hyaluronan: An overview" *Immunol. Cell Biol.* 74: A1-A7, 1996.

Knudson, C., "Hyaluronan receptor-directed assembly of chondrocyte pericellular matrix" *J Cell Biol.* vol. 120, No. 3: 825-834, Feb. 1993.

Knudson, C., Knudson, W., "Hyaluronan-binding proteins in development, tissue homeostasis, and disease" *FASEB* vol. 7: 1233-1241, Oct. 1993.

Entwistle, J., Hall, C.L., Turley, E.A. "Hyaluronan receptors: Regulators of signaling to the cytoskeleton" *J Cell. Biochem.* 61: 569-577, 1996.

Knudson, W., Biswas, C., Li, X., Nemec, R.E., Toole, B.P. "The role and regulation of tumour-associated hyaluronan" *Ciba Found Symp.* 143: 150-169, 1989.

Zeng, C., Toole, B.P., Kinney, S.D., Kuo, J., Stamenkovic, I., "Inhibition of tumor growth in vivo by hyaluronan oligomers" *Int. J. Cancer 77*: 396-401, 1998.

Brekke, J.H. "Architectural principles applied to three-dimensional therapeutic implants composed of bioresorbable polymers" In Wise, D., et al., eds., Encyclopedic Handbook of Biomaterials and Bioengineering, vol. 1. New York: Marcel Dekker, 1995, pp. 689-731.

Li, C., Yu, D-F., Newman, R.A., Millas, L., Hunter, N.R., Wallace, S. "Development of a highly efficacious water-soluble polymer-taxol conjugate" *Proc. Annu. Meet. Am. Assoc. Cancer Res.* 1731: A, 1997.

Greenwald, R.B., Gilbert, C.W., Pendri, A., Conover, C.D., Xia, J., Martinez, A. "Drug delivery systems: water soluble taxol 2'-poly-(ethylene glycol) ester prodrugs—design and in vivo effectiveness" *J. Med. Chem.* vol. 39, No. 2: 424-431, 1996.

Zignani, M., Merkli, A., Sintzel, M.B., Bernatchez, S.F., Kloeti, W., Heller, J., Tabatabay, C., Gurny, R., "New generation of poly (ortho esters): synthesis, characterization, kinetics, sterilization and biocompatibility" *J. Control Release* 48: 115-129, 1997.

Ma, P.X., Zhang, R., Xiao, G., Franceschi, R., "Engineering new bone tissue in vitro on highly porous poly($\alpha$-hydroxyl acids)/hydroxyapatite composite scaffolds" *J. Biomed. Mater. Res.*, 54: 284-293, 2001.

Brown, T.J., Laurent, U.B.G., Fraser, J.R.E,, "Turnover of hyaluronan in synovial joints: elimination of labeled hyaluronan from the knee joint of the rabbit" *Exp. Physiol.* 76(1): 125-134, 1991.

Fraser, J.R.E., Laurent, T.C., Laurent, U.B.G., "Hyaluronan: its nature, distribution, functions and turnover" *J. Intern. Med.* 242(1): 27-33, 1997.

Vernino, A.R., Wang, H.L., Rapley, J., Nechamkin, S.J., Ringeisen, T.A., Derhalli, M., Brekke, J., "Use of biodegradable polylactic acid barrier materials in the treatment of grade II periodontal furcation defects in humans—part I: a multi-center investigative surgical study" *Int. J. Periodontics Restorative Dent.* vol. 18, No. 6: 573-585, 1998.

Vernino, A, Wang, H.L., Rapley, I., Nechamkin, S.J., Ringeisen, T.A., Derhalli, M., Brekke, J., "The use of biodegradable polylactic acid barrier materials in the treatment of grade II periodontal furcation defects in humans—part II: a multi-center investigative surgical study" *Int. J. Periodontics Restorative Dent.* vol. 19, No. 1: 57-65, 1999.

Chu, R.C., Coutts, R.D., Yoshioka, M., Harwood, F.L., Monosov, A.Z., Amiel, D., "Articular cartilage repair using allogeneic perichondrocyte-seeded biodegradable porous polylactic acid (PLA): a tissue engineering study" *J. Bio. Mat. Res.* 29: 1147-1154, 1995.

Vogelin, E., Jones, N.F., Huang, J.I., Brekke, J.H., Toth, J.M., "Practical illustrations in tissue engineering: Surgical considerations relevant to the implantation of osteoconductive devices" *Tissue Eng.* vol. 6, No. 4: 449-460, 2000.

Brauker, J.H., Carr-Brendel, V.E., Martinson, L.A., Crudele, J., Johnston, W.D., Johnson, R.C., "Neovascularization of synthetic membranes directed by membrane microarchitecture" *J. Biomed. Mater. Res.* vol. 29: 1517-1524, 1995.

van Dorp, A.G.M., Verhoeven, M.H.C., van Blitterswijk, C.A., Ponec, M., "A keratinocyte and fibroblast populated biodegradable copolymer: a three-dimensional skin equivalent" 20th Annual Meeting of the Society for Biomaterials, Boston, MA Apr. 5-9, 1994.

Chirila, T.V, Constable, I.J., Crawford, G.J., Vijayasekaran, S., Thompson, D.E., Chen Y., Fletcher, W.A., "Poly(2-hydroxyethyl methacrylate) sponges as implant materials: in vivo and in vitro evaluation of cellular invasion" *Biomaterials*, vol. 14 No. 1: 26-38, 1993.

Dernell, W.S., Wheaton, L.G., Gavin, P.R., Leathers, C.W., Leid, R.W., "Thromboxane as a measure of cutaneous vascular damage following irradiation" *Plast. Reconstr. Surg.*, 93, No. 7: 1465-1472, Jun. 1994.

Luo Y., Bernshaw, N. J., Lu, Z.-R., Kopecek, J., and Prestwich, G. D.: Targeted delivery of doxorubicin by HPMA copolymer-hyaluronan bioconjugates, Pharamaceutical Res., 19(4): 396-402, 2002.

Dosio, F., Brusa, P., Crosasso, P., Arpicco, S., Cattel, L.: Preparation, characterization and properties in vitro and in vivo of a paclitaxel—albumin conjugate. J. Cont Rel, 47: 293-304, 1997.

Brekke, J.H.: A rationale for delivery of osteoinductive proteins. Tissue Eng. 2(2): 97-114, 1996.

Memorial Sloan-Kettering Cancer Center http://www.mskcc.org/mskcc/html/1879.cfm (2 pages).

Reuters Business Insight Healthcare, Therapeutic Report Series: The Cancer Outlook to 2007, pp. 1-210, 2002.

Coughlin C.T., Richmond, R.C.: Biologic and clinical developments of cisplatin combined with radiation: concepts, utility, projections for new trials, and the emergence of carboplatin, Semin Oncol, 16: 31-43, 1989.

Tri-Network Health Desk http://www.tri-network.net/health.html (2 pages), date unavailable.

* cited by examiner

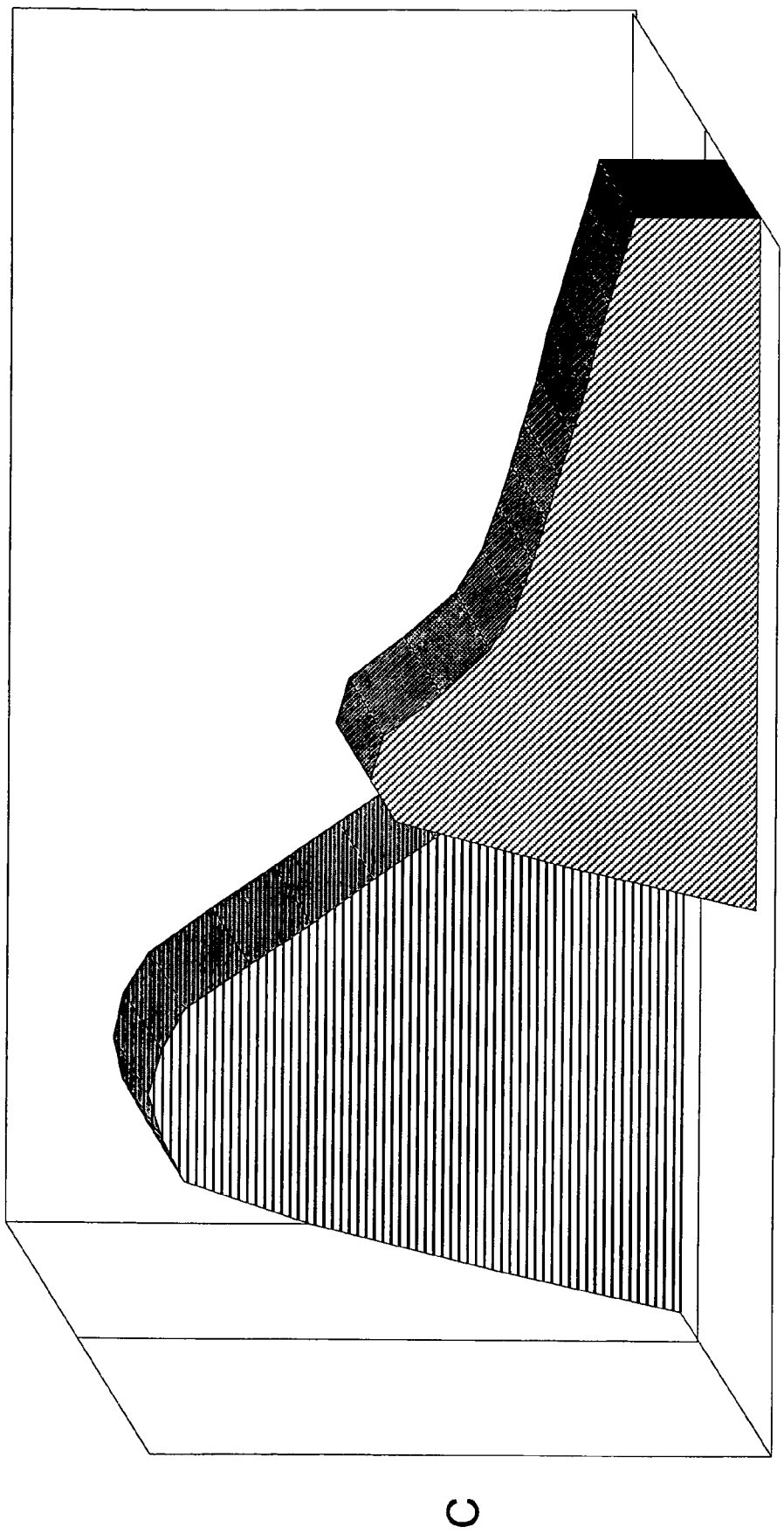

DEVICE AND METHODS FOR SEQUENTIAL, REGIONAL DELIVERY OF MULTIPLE CYTOTOXIC AGENTS AND DIRECTED ASSEMBLY OF WOUND REPAIR TISSUES

BACKGROUND

The present invention generally relates to devices and methods for treatment of cancer and particularly breast cancer and specifically to devices and methods for the regional delivery of multiple cytotoxic agents in a programmable, sequential manner and for the directed assembly of wound repair tissues.

Every adult is at risk for breast cancer. One in nine women who live to the age of 90 will be treated for breast cancer at some time in her life, and more than 180,000 women in the United States were diagnosed with the disease in 2000. Although breast cancer is rare in men, it does occur: an estimated 1,400 cases will be diagnosed in American men in the year 2002. In 1999, approximately 43,000 women died from the disease according to the American Cancer Society. Breast cancer is the most common form of cancer in women and ranks as the second leading cause of cancer deaths among women of all ages. Breast cancer is the number one cause of cancer death for women aged 29-59.

Despite the development of innovative systemic medical therapies for the treatment of breast cancer, local disease control is still a problem. This is also true for other common malignancies such as prostatic carcinoma and colon cancer. Under most current systemic therapy protocols, chemotherapeutic drugs are given to patients systemically as an adjunct to the removal of malignant tumors. Even with preoperative and postoperative radiation therapy, local recurrences often develop. Because of the toxicity of the drugs, the attainable concentration of an active drug in the tumor after systemically-administered chemotherapy is, in part, restricted by the dose-limiting systemic toxicity tolerated by the body. Preoperative high dose chemotherapy or radiation therapy can adversely affect normal tissue healing, add morbidity and expense and may allow primary tumors that are insensitive to preoperative treatment an opportunity to extend locally, to distant sites, or both.

Breast cancer can be detected at an early treatable stage. Five year survival after treatment for early-stage breast cancer is 97%. The basis for contemporary breast cancer treatment dates back to the 1890s when William Halsted developed the radical mastectomy; a technique for removing a breast, the underlying chest muscle and the lymph nodes in the armpit. According to Halsted, breast cancer could be cured by carving a wide clearance around the initial tumor and its draining sites leaving clear margins of healthy tissue. Today, a modified radical mastectomy with preservation of the pectoral muscles, a somewhat less severe version of the Halsted operation, is still used in approximately 66% of breast cancer surgeries.

While modified radical mastectomy remains the dominant form of treatment for early cancer of the breast, a much less drastic operation called a lumpectomy (sometimes also called breast conserving therapy) combined with radiation therapy has recently been adopted and is used in a third of tumor removal surgeries. As the name suggests, a lumpectomy procedure involves only the removal of the tumor along with a "shell" of healthy tissue to ensure that the whole tumor is taken. There is clear evidence that a lumpectomy, when followed by radiation therapy, is just as effective as the modified radical mastectomy in most situations.

According to the New England Journal of Medicine, radiation following lumpectomy resulted in a five-year survival rate of 85 percent, as compared with 76 percent with total mastectomy. At eight years, 90 percent remained free of ipsilateral breast tumor as compared to 61 percent of those not treated with irradiation after lumpectomy. Radiation, however, has no known effect on distant metastases which are the chief sources of danger.

Any improvement in the treatment of breast cancer will probably come from chemotherapy. Used as an adjuvant therapy to surgery, chemotherapeutic compounds kill cancer cells including any metastases lurking in the body. Because of the side effects of the agents, chemotherapy, until recently, was a treatment of last resort, administered only to patients with extensive metastatic disease. Even today, despite discoveries that moderate side effects, chemotherapy is not easy for the patient. Chemotherapy for breast cancer is usually given in the form of a multi-drug regimen, one the most common being cyclophosphamide, doxorubicin and 5-fluorouracil.

Sustained or controlled release of chemotherapeutic drugs directly into wounds after the removal of high grade malignancies may provide control of microscopic residual cancer cells and avoid system toxicity and wound healing problems while allowing early ablative surgery with the preservation of function of the formerly diseased area. To this end, the controlled delivery of bioactive agents from polymeric materials has attracted considerable attention of investigators throughout the scientific community for more than two decades. The trend in drug delivery technology has been toward bioresorbable polymer excipients requiring no follow-up surgical removal once the drug supply is depleted. Such polymers offer the great advantage of enabling either site-specific or systemic administration of pharmaceutical agents.

Specifically, bioresorbable polymer technologies have been developed for targeted and controlled drug delivery of chemotherapeutic drugs to treat cancer. Most of these polymer delivery systems are based on gel, nanoparticals or microsphere technology for administration via intravenous injection. Others are solid or architecturally ill-defined polymer wafers and blocks that require surgical implantation.

The devices of U.S. Pat. Nos. 5,855,608; 5,981,825; and 6,264,701, each of which are incorporated herein by reference and hereinafter referenced to as the OPLA matrix, have proven to produce tissue engineering constructs capable of directing the formation of single or multiple functional tissues in bone, cartilage and soft tissue applications. Study has occurred in the canine osteosarcoma model of the use of the OPLA matrix joined to Cis-diamminedichloroplatinum II (CDDP; cisplatin; Platinol™, hereinafter cisplatin). Cisplatin is a heavy metal complex agent that has been used for many years in chemotherapy protocols. The resulting chemotherapy delivery system provided initially high local concentrations followed by a lower but sustained systemic delivery of cisplatin at therapeutic doses and showed efficacy from the standpoint of local primary tumor control and control of occult metastatic disease. Specifically, the chemotherapy delivery system consisted of a porous body implant defined by an internal architecture of partially enclosed, randomly sized, shaped and positioned intercommunicating interstices. The cisplatin is joined to the polymer during manufacturing yielding 8% cisplatin by weight of total polymer. Sterilization is achieved by exposure of the finished chemotherapy delivery system to 2.5 Mrads of gamma irradiation. The hypothesis of the chemotherapy delivery system is that a low but sustained therapeutic dose of cisplatin will decrease system toxicity while delaying or preventing distant metastasis.

Pharmacokinetic and local/systemic effect studies conducted on the chemotherapy delivery system device documented that except for some mild, self-limiting swelling and edema of soft tissue at the surgery site, no overt systemic or local clinical toxicity was detected with the chemotherapy delivery system. The usual maximum dose-limiting schedule for cisplatin given intravenously to dogs is 70 mg/m$^2$. The dose with the chemotherapy delivery system exceeded the maximum dose-limitation by approximately 16.5% without clinically detectable systemic toxicity. The peak serum dose of platinum from the chemotherapy delivery system was 20% of that seen with a similar intravenous dose. The area under the curve for total serum platinum concentration with the chemotherapy delivery system was shown to be 27 times that of a similar dose of intravenous platinum. Toxicity to bone marrow, kidney, nervous tissue or any other organ was negligible and the chemotherapy delivery system provided higher total sustained levels of the drug with less systemic toxicity than can be achieved by intermittent intravenous administration.

Thus, a need continues to exist for devices and methods for delivering cytotoxic agents which overcome the shortcomings and deficiencies of the prior art.

SUMMARY

The present invention solves this need and other problems in the delivery of cytotoxic agents and involves the novel regional delivery of cytotoxic agents utilizing the OPLA matrix for extending the life-table of the population receiving this therapy while reducing the incidence of metastasis and delaying the onset of first metastasis and while providing higher total sustained levels of drug with less system toxicity than can be achieved by intermittent intravenous administration. The device of the present invention integrates disparate properties into a single construct capable of the following pharmacologic and tissue regeneration functions:

1. High concentration, regional delivery of multiple cytotoxic agents in a predetermined sequence.
2. Release of cytotoxic agents at a rate and concentration optimized for synergistic therapeutic effect with radiation therapy applied at an intensity and total quantity less than that required for a comparable effect if used alone (independently of the cytotoxic agents).
3. Direct final deposition and morphology of fibrous (scar) tissue that is the repair tissue for the defect created by surgical excision of the offending tumor.

In preferred aspects, the present invention utilizes bioresorbable devices for targeted and controlled drug delivery of chemotherapeutic drugs to treat cancer and in the most preferred form to treat breast cancer. In most preferred aspects, the bioresorbable delivery device has a gross size, shape, architecture and mechanical characteristics to encourage regeneration of surgically removed tissue and restoring normal tissue contours and consistency. Additionally, the bioresorbable delivery device provides a depot for multiple cytotoxic agents which have different mechanisms of antitumor activity actions and which cooperate together and with radiotherapy in the treatment of cancer, with the cytotoxic agents being delivered sequentially in a programmable manner that maximizes their treatment cooperation. In further preferred aspects of the present invention, the bioresorbable delivery device provides a novel delivery vehicle for the cytotoxic agent paclitaxel which was previously intravenously administered.

The present invention will become clearer in light of the following detailed description of an illustrative embodiment of this invention described in connection with the drawings.

DESCRIPTION OF THE DRAWINGS

The illustrative embodiment may best be described by reference to the accompanying drawings where:

FIG. 1 shows a graphical depiction having an axis labeled C depicting the serum drug concentration (ug/ml) and having an axis labeled T depicting time (post implantation), with the volume under the curve depicted by lines parallel to the T axis depicting the release of paclitaxel while the volume under the curve depicted by angled lines depicting the release of cisplatin.

DESCRIPTION OF THE ILLUSTRATIVE EMBODIMENT

The device of the present invention is built upon the macrostructure/microstructure strategy of the OPLA matrix previously used to good advantage for the presentation of biological modifiers such as bone morphogenetic proteins. The purposes of the macrostructure for the device of the present invention are three-fold: (i) establish gross size and shape of the device to provide soft tissue support as well as essential mechanical characteristics to prevent soft tissue prolapse; (ii) establish and maintain 3-D architecture internally of the device for soft tissue in growth, organization and stabilization following drug release; and (iii) function as the reservoir (or depot) for a first cytotoxic agent, which in the most preferred form is cisplatin. The macrostructure of the device is fabricated of a structural, biodegradable polymer selected from the group of poly (alphahydroxy acids) and in the most preferred form of D,D-L,L-polylactic acid (PLA) from a solution of the polymer in organic solvent by means of solid-liquid phase separation through freezing and subsequent lyophilization. The device can be produced having a three-dimensional architecture whose internal 3-D geometry is customized to match that of the recipient tissue. The first cytotoxic agent such as cisplatin is embedded between PLA polymer chains at fabrication by admixing the first cytotoxic agent into the polymer/solvent solution prior to lyophilization. By carefully controlling the thermal and mechanical profiles of the fabrication process, the bulk of the cisplatin particles will be sequestered immediately beneath the surface of the macrostructure's partitions.

Suspended within the interstices of the device's macrostructure (but remaining independent of the macrostructure material) is the device's microstructure. In the most preferred form, the microstructure is a velour of hyaluronan (HY), but other biologically inert materials such as alginate or chitosan may provide an alternate strategy. Specifically, in the most preferred form, the microstructure is formed by lyophilization of an HY water solution after it has been invested within the interstices of the OPLA macrostructure. In both the dry and hydrated states, the OPLA macrostructure and HY microstructure remain physically separate entities. The purposes of the microstructure are three-fold: (i) provide the ligand for a second cytotoxic agent, which in the preferred form is paclitaxel, thus rendering the second cytotoxic agent water soluble; (ii) function as the water reservoir of the device, while simultaneously inhibiting the macrostructure polymer from gaining access to water during the early post-implantation period; and (iii) provide controlled release for the second cytotoxic agent as well as establishing the sequencing of cytotoxic agent release into tissue and particularly release of the cytotoxic agent of the microstructure first followed by the release of the cytotoxic agent of the macrostructure second. (FIG. 1)

Hyaluronic acid (HY) is a naturally occurring mucopolysaccharide found in all mammalian and non-mammalian species. HY plays multiple fundamental roles critical to various biological processes including those of inflammation, cell proliferation and migration during embryogenesis as well as early wound healing and remodeling of healthy tissues. These functions are made possible by interaction of the CD44 cell surface receptor with hyaluronic acid as its ligand. Malignant tumor cells synthesize large quantities of hyaluronic acid and overexpress CD44 receptors in order to utilize HY as a chemotactic ground substance for regional invasion of adjacent healthy tissue. Oligomers and low molecular weight polymers of HY have both exhibited anti-tumor activity by competitively inhibiting binding of the tumor cell's CD44 receptors to high molecular weight HY of the extracellular matrix (ECM). Joining anti-tumor agents to HY specifically targets aggressively growing malignant cells by being incorporated into the cell via its CD44 receptor complex.

These attributes of HY, as well as its immunoneutrality, make it the material of choice to function as the delivery vehicle for a second cytotoxic agent whose mechanism of action is different from, but complimentary to, that of the first cytotoxic agent. Specifically, in the preferred form, the platinum of cisplatin damages a cell's deoxyribonucleic acid (DNA) ability to replicate itself accurately, while the second cytotoxic agent in the preferred form of paclitaxel paralyzes the cell's cytoskeleton, as described below.

Microtubules are protein polymers of the cell's cytoskeleton that provide compressive strength to the cell by resisting the forces generated by contractile elements of the cytoskeleton (i.e. actin). Microtubules are an assemblage of heterodimers composed of α-tubulin and β-tubulin. Under normal conditions, a cell's microtubules are continuously and rapidly polymerized and depolymerized in response to the cell's interaction with its extracellular matrix (ECM) or its progression through mitosis. Paclitaxel binds tightly to microtubules of the cell's cytoskeleton, thereby stabilizing them and preventing their rapid depolymerization. Paclitaxel also causes much of the cell's free tubulin to assemble into stabilized microtubules whether or not they contribute to the cell's overall physiologic functioning. Under the influence of paclitaxel, therefore, the cell's cytoskeleton is paralyzed, unable to move through its ECM and unable to replicate itself through cell division.

Paclitaxel, *Taxus brevifolia* (trademark Taxol®, a product of Bristol-Myers Squibb, herewith paclitaxel) is a natural product with anti-tumor activity that is derived from the bark of the Pacific yew tree. Though paclitaxel is approved by the US Food and Drug Administration (FDA) for use in treatment of several malignancies, its clinical application has been limited due to its poor aqueous solubility and the toxic effects associated with its excipient, Cremophor EL (polyoxyethylated castor oil). There have been multiple attempts to incorporate paclitaxel into several other (less toxic) materials including poly(L-glutamic acid), albumin, poly (ethylene glycol) derivatives, and HY.

The articles of Pouyani T and Prestwich G D: *Functionalized derivatives of hyaluronic acid oligosaccharides: Drug carriers and novel biomaterials*. Bioconjugate Chem., 5:339-347, 1994; and Luo T, Bemshaw N. J., Lu Z-R, Kopeck J, and Prestwich G D: *Targeted delivery of doxorubicin by HPMA copolymer-hyaluronan bioconjugates*. Pharmaceutical Res, 19(4):396-402, 2002, recognizes the conjugation of hyaluronic acid with cytotoxic agents as a means for their delivery and controlled release. The protocol for synthesis of a low molecular weight hyaluronic acid (LWHA)—paclitaxel conjugate adapted from those described by Luo and Prestwich is as follows:

LWHA (Mw<$5\times10^3$) is obtained by the degradation of high molecular weight HY material with a molecular weight of approximately $1.6\times10^6$. Molecular weight degradation is accomplished using testicular bovine hyaluronidase (degradation verified by GPC analysis). Adipic dihydrazido functionalized LWHA is prepared by the addition of adipic dihydrazine at the carboxylate moiety. Adipic dihydrazine requires minimally aggressive reaction conditions (LWHA is not degraded further and does not cross-link during the coupling of the adipic dihydrazine). Coupling of adipic dihydrazine to the carboxylate moiety of LWHA is performed at pH 4.75 (optimal pH for carbodiimide coupling reactions) using 1-[3(Dimethylamino)propyl]-3-ethylcarbodiimide hydrochloride as an initiator. The resultant pendant hydrazido group is sufficiently reactive and readily available (stearic effects are mitigated by having the hydrazido group remote from the LWHA backbone) to react with other compounds. LWHA and the adipic dihydrazido functionalized LWHA are purified by dialysis (3500 Mw cutoff membrane used) and purity is documented by GPC instrumentation.

Paclitaxel is prepared for conjugation with the adipic dihydrazide functionalized LWHA by first synthesizing the N-hydroxysuccinimide ester. This is accomplished by first reacting N-hydroxysuccinimide with diphenylphosphoryl chloride to yield N-hydroxysuccinimido diphenyl phosphate, which is then reacted with paclitaxel hemisuccinate (previously synthesized from paclitaxel and succinic anhydride) to form the paclitaxel-NHS ester. Adipic dihydrazido functionalized LWHA is reacted with paclitaxel-NHS ester via the free pendant hydrazido moiety and the carboxylate moiety of the succinate group.

Prior art teaches use of very low molecular weight hyaluronan fractions as the ligand for paclitaxel (Mw<$5\times10^3$). The invention of this patent employs a conjugate including hyaluronic acid of substantially higher molecular weight (Mw=$40$–$60\times10^3$) and in the most preferred form blended with pure, high molecular weight hyaluronic acid (Mw>$1\times10^6$) at a mass ratio in the order of 1:1 in the preferred form. Thus, the present invention accomplishes two functions ignored by prior art. 1) Varying the molecular weight of HY in the HY-paclitaxel conjugate provides a control for the rate at which the conjugate is released into adjacent tissues. 2) Having a substantial fraction of the HY ligand present at molecular weights of 50,000 (+/−) provides a convenient chemotactic ground substance for tumor cells remaining in adjacent tissues; thus making the implant an attractive, but lethal destination for these tumor cells. 3) Finally, blending the HY-paclitaxel conjugate with a pure HY moiety of high molecular weight provides the microstructure with an additional pharmacokinetic control mechanism as well as enhanced chemotactic potential for tumor cells remaining in adjacent tissues. The HY-paclitaxel microstructure is incorporated into all cells expressing the CD44 receptor. Malignant tumor cells overexpress the CD44 receptor as well as large quantities of hyaluronic acid, using binding of CD44 to the HY ligand as their primary mechanism for invading adjacent normal tissues. The HY-paclitaxel microstructure is endocytosed by the cell via its CD44 receptors followed by hydrolytic cleavage of the bioconjugate's 2' ester linkage (presumably through acid hydrolysis by lysosomal enzymes) and release of the pharmacologically active drug. All cells in the region expressing the CD44 receptor will ingest some of the bioconjugate. No matter which cells ingest the bioconjugate, the HY-paclitaxel complex cannot escape being endocytosed and metabolized to extinction. Malignant tumor cells in the region will selectively ingest proportionally more of the bioconjugate than will normal connective tissue or mesenchymal cells due to their overexpression of the CD44 receptor.

The whole process of liberating the cytotoxic agents from their depot-materials is water dependent. Hyaluronic acid is aggressively hydrophilic and can bind water to a mass ratio of 1,000:1. Furthermore, the viscoelastic properties of an HY solution trap the solution's water moiety, thus preventing any adjacent material from gaining access to it. Polylactic acid is inherently hydrophobic and repels water. Once the device is implanted, the microstructure of HY will accept wound fluids in quantity because of its strong hydrophilic quality and, consequently, starve the polymer macrostructure of fluids. The rate at which the second cytotoxic agent which in the preferred form is paclitaxel is released and the time interval before the first cytotoxic agent which in the preferred form is cisplatin is first exposed to the tissues is controlled by the initial weight average molecular weight of the HY as well as by its mass:volume concentration. The delay time for exposure of the first cytotoxic agent is a function of HY's viscoelastic properties. These properties are reduced as the molecular weight of hyaluronan is reduced, secondary to endocytosis of the HY-paclitaxel by tumor cells. At a certain molecular weight, the microstructure's (HY) viscoelastic properties are reduced to the point at which it begins to (progressively) release its retained water (est. 12-14 hours post implantation); thus making free water available to the polymer of the macrostructure (depot for the first cytotoxic agent).

When any polymer of the poly(alpha-hydroxy acid) group comes into contact with water, water molecules slowly infiltrate between its polymer chains, thus creating microporosities between the polymer chains. When enough water is imbibed by the polymer, microchannels are created between the polymer chains and any drug cargo processed into the polymer is provided with both a channel and a medium for escape. In vitro data demonstrates that approximately 35-45 percent of the mass of the first cytotoxic agent is released within the first 18 hours following exposure to fluids. Further, 70-90 percent of the mass of the first cytotoxic agent is released within the first 28 days and before molecular degradation of the polymer becomes evident. The remaining cargo of the first cytotoxic agent resident within the OPLA macrostructure will be released into tissue as the molecular weight of the polymer is reduced but prior to significant depreciation of the polymer's mechanical properties.

One goal of the device of the most preferred form of the present invention is to present the first cytotoxic agent at relatively high local concentrations for a period of time. This level of concentration provides the opportunity to employ the synergistic therapeutic effects in the most preferred form of cisplatin and radiotherapy. It is believed that cisplatin is useful as a radiation sensitizer. To this end, the area under the curve for cisplatin emanating from the device of the present invention will be low enough to avoid any normal tissue toxicity, but high enough to express its synergistic therapeutic properties with radiotherapy. The cisplatin concentration and radiotherapy intensity can be calibrated against each other so that the wound's collateral circulation is not irreversibly damaged. According to the preferred teachings of the present invention, the regional delivery of cisplatin in the concentration provided by the delivery system of the present invention produces synergistic therapeutic properties when utilized with radiotherapy in breast-conserving treatment protocols.

After the cytotoxic agents incorporated into the device of the present invention have been deployed, the device (ie. the remaining 3-D macrostructure) will be available for the final purpose of tissue engineering. The polymer of the OPLA macrostructure can be engineered to maintain its internal, three-dimensional spatial arrangements and significant mechanical properties for a prolonged period of time post-implantation to support endothelial budding and repopulation of the device by fibroblasts. The internal, 3-D geometry of the matrix will dictate location of cells and collateral circulation, thereby dictating the final shape and intimate interactions of individual cicatrix strands of scar tissue within its boundaries. Since the gross size and shape of the device can be customized for each wound site, this predetermined organization of scar tissue will be the final legacy left after the macrostructure has been fully hydrolyzed to extinction.

In a normal healing milieu, scar tissue grows in parallel bundles of fibers and then contracts at several disparate time periods. This often results in a "balling" up of the tissue giving it a consistency different from that of the original tissue. The macrostructure polymer should remain intact long enough after its drug cargo has been dispensed to dictate the shape and intimate interactions of the individual scar tissue fibers deposited throughout the site of implantation. Cells growing into the matrix are prevented from creating parallel bundles by the polymer's architecture and are, instead, chaotically arranged. During the early periods of scar contracture, the polymer is present to provide mechanical resistance to force vectors generated by myofibroblasts of scar tissue. Later contraction is limited by the cancelling forces of the chaotic tissue arrangement. The result is a final soft tissue that is more normal in appearance and provided without the aid of proteins.

To achieve the desired tissue engineering result, it is important that the polymer matrix retain its mechanical characteristics and support its three-dimensional architecture long enough to operate as an in vivo cell culture substratum for cell infiltration, growth and maturation. This is a function of the structural polymer's molecular weight (Mw), degree of crystallinity, hydrolysis profile and partition thickness. These characteristics can be controlled through selection of polymer species, prefabrication Mw, method of fabrication and choice of sterilization agent.

D,D-L,L-polylactic acid is amorphous (non-crystalline) at Mws above 5,000. Therefore, the rate of hydrolysis throughout the macrostructure is uniform. An in vitro hydrolysis study of D,D-L,L-polylactic acid with a post-sterilization Mw of 135,000 demonstrated that the macrostructure architecture remained intact until the polymer's Mw is reduced below 20,000, with it taking about six months to reduce the polymer molecular weight below 20,000. It should be appreciated that it is contemplated that D,D-L,L-polylactic acid of high MW in the range of 500,000-600,000 will be utilized to construct the device of the present invention.

The method of sterilization is also an important consideration in engineering the polymer to remain porous for a sufficient period of time after implantation. This is because the sterilization method can affect a change in the polymer Mw profile. Gas plasma technology provides a method of sterilization that employs an ionized or partially ionized gas for its biocidal agents. Gas plasmas, together with electromagnetic and ultraviolet radiation and other reactive charged particles are generated through the action of high-temperature or strong electromagnetic fields on gases. The preferred gas plasma sterilization process separates stable charged biocidal particles from the electromagnetic/ultraviolet radiation, electrons, and ions formed along with them. Therefore, starting at a high Mw of greater than 500,000, the length of time required for tissue fluids to hydrolyze the polymer will be proportionally greater than that demonstrated in the in vitro hydrolysis study. Consequently, the mechanical and architectural properties will remain intact for a protracted period of time following elution of the cytotoxic agents in the delivery system of the present invention.

Autocatylatic, acid hydrolysis of polylactic acid is a phenomenon in which the central portions of large, solid constructs are degraded more rapidly than surface polymer exposed to interstitial fluids. When this occurs, there is a catastrophic collapse of the device once its "skin" of polymer has been sufficiently weakened. A PLA device susceptible to this phenomenon would be unacceptable as a drug delivery vehicle since the unpredictable collapse of the unit would alter the predetermined drug pharmacokinetics. Polymer partitions of OPLA are not susceptible to the bi-phasic polymer hydrolysis phenomenon demonstrated for massive (bulk or solid) devices because the partitions are less than 100 μm in thickness. Therefore, they are incapable of supporting the autocatalytic, acid hydrolysis produced in devices with polymer thicknesses greater than 100 μm. The practical consequences of this distinction is that the structural partitions of the OPLA structure cannot collapse upon themselves.

The distinguishing features of the present invention over the prior art include:

1. The device of the present invention is fabricated as a dry solid and can be applied only as a surgical implant. In prior art describing bioconjugates of low molecular weight hyaluronic acid with cytotoxic agents, the resulting HY-drug complex is designed to improve solubility of the cytotoxic agent and facilitate its intravenous administration. Conjugation of a cytotoxic agent to high molecular weight hyaluronic acid does render the complex hydrophilic, but it precludes its intravenous administration.

Though the high molecular weight HY-paclitaxel bioconjugate and blend of the present invention renders the paclitaxel water soluble, the HY also functions as a chemotactic ground substance to attract tumor cells into the construct and thus into intimate contact with the cytotoxic agents contained therein.

2. Hyaluronic acid is employed of relatively high weight average molecular weight ($Mw=40-60\times10^3$). All prior art involving bioconjugates of hyaluronic acid with cytotoxic agents teaches use of very low molecular weight examples of hyaluronan ranging from oliogosaccharides of $Mw<5\times10^3$.
3. In previous patents, Brekke teaches use of hyaluronic acid to deliver "therapeutic agents" to surgically created wounds. While Brekke specifies in detail the possible physical locations for these agents within the device, the association of the therapeutic agents with the macro- and microstructure materials is limited to that of a passive cargo; one that does not chemically interact with the material of either the macrostructure nor the microstructure.

In the construct of the preferred form of the present invention, the first cytotoxic agent which is cisplatin in the most preferred form is a passive cargo residing between the polymer chains of the macrostructure (U.S. Pat. No. 4,186,448—Device and Method for Treating and Healing A Newly Created Bone Void, which is incorporated herein by reference). However, the second cytotoxic agent which is paclitaxel of the preferred form of the present invention is chemically bound to the high molecular weight hyaluronic acid of the microstructure.

4. Prior art describing HY-drug bioconjugates does not anticipate a formulation in which the HY-drug bioconjugate is combined with a second drug.
5. Neither Brekke nor the prior art describing HY-drug bioconjugates anticipate a device:
   a. in which the HY-drug bioconjugate is but one of a multiplicity of drug delivery vehicles; or
   b. is capable of releasing its various cargos in a predetermined and coordinated chronologic sequence and in the most preferred form at initially high local concentrations followed by a lower but sustained systemic delivery at therapeutic doses.
6. The device of the present invention anticipates the macrostructure of the drug delivery system (OPLA) functioning as a tissue engineering device in order to dictate the final three-dimensional morphology of repair fibrous connective tissue (scar tissue).
7. Though cisplatin is a powerful cytotoxic agent in its own right, it is used in the present invention for its ability to act synergistically with radiotherapy (X-ray therapy). By taking advantage of this fact, the device described in this patent allows a third treatment modality (X-ray therapy) to be introduced into the diseased tissues. X-rays are lethal to rapidly dividing cells because it damages the cell's ability to repair damaged DNA and reconstitute single strands of DNA into the normal double helix. When postoperative serum levels of cisplatin reach the appropriate concentration, radiotherapy to the tumor site is begun. In the most preferred form, radiotherapy is begun immediately after release of paclitaxel has been completed, while cisplatin is being released, but after the initial release of high local concentrations of the cisplatin. At this point, and simultaneously, remaining tumor cells are being paralyzed by paclitaxel, replication of their DNA is being impaired by cisplatin and repair/reconstitution of damaged or replicating DNA is being inhibited by X-radiation energy.
8. The device according to the preferred teachings of the present invention anticipates using the molecular weight of the hyaluronic acid ligand (for the HY-paclitaxel conjugate and blend) as a means to control the pharmacokinetics of paclitaxel exposure to tumor cells.

Now that the basic teachings of the present invention have been explained, many extensions and variations will be obvious to one having ordinary skill in the related technologies. For example, although the device of the present invention has been described in its most preferred form including several unique features believed to produce synergistic results, such features can be utilized singly in other combinations according to the teachings of the present invention.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. Cancer treatment method comprising:
   implanting a bioresorbable delivery system into tissue containing one or more cancers selected from the group consisting of breast cancer, prostate cancer and colon cancer for releasing first and second cytotoxic agents in a predetermined chronologic sequence with the first cytotoxic agent being released first followed by release of the second cytotoxic agent; and
   radiating the wound during release of the second cytotoxic agent and after initial release of the first cytotoxic agent, wherein said implanting and radiating effectively treats the one or more cancers.

2. The cancer treatment method of claim 1 with the first and second cytotoxic agents being each released initially at high local concentrations followed by a lower but sustained systemic release.

3. The cancer treatment method of claim 2 with the first cytotoxic agent adapted to paralyze a cell's cyctoskeleton and with the second cytotoxic agent adapted to damage a cell's ability to accurately replicate, with radiating damaging a cell's ability to repair damaged DNA.

4. The cancer treatment method of claim 2 with the first cytotoxic agent being paclitaxel and with the second cytotoxic agent being cisplatin.

5. The cancer treatment method of claim 1 wherein the bioresorbable delivery system comprises a first bioresorbable delivery vehicle which is hydrophobic, with the second cytotoxic agent different from but complimentary to the first cytotoxic agent, with the first cytotoxic agent being a cargo in the first bioresorbable vehicle for delivery of the first cytotoxic agent during resorption of the first bioresorbable delivery vehicle, with the first bioresorbable vehicle including void spaces; a second bioresorbable delivery vehicle which is hydrophilic, with the second cytotoxic agent being a cargo in the second bioresorbable vehicle for delivery of the second cytotoxic agent during resorption of the second bioresorbable delivery vehicle, with the second bioresorbable delivery vehicle and the second cytotoxic agent located in the void spaces of the first bioresorbable delivery vehicle.

6. The cancer treatment method of claim 5 further comprising chemically binding the second cytotoxic agent to the second bioresorbable delivery vehicle.

7. The cancer treatment method of claim 6 further comprising conjugating the second bioresorbable delivery vehicle to the second cytotoxic agent.

8. The cancer treatment method of claim 7 wherein the second bioresorbable delivery vehicle comprises hyaluronic acid.

9. The cancer treatment method of claim 8 with the hyaluronic acid having a high molecular weight.

10. The cancer treatment method of claim 7 with the second cytotoxic agent being paclitaxel.

11. The cancer treatment method of claim 10 with the first cytotoxic agent being cisplatin.

12. The cancer treatment method of claim 11 further comprising defining the void spaces of the first bioresorbable delivery vehicle by an internal architecture of partially enclosed, randomly sized, shaped and positioned intercommunicating interstices dictating a final three-dimensional morphology of repair tissue.

13. The cancer treatment method of claim 12 with the first bioresorbable delivery vehicle being formed of a bioresorbable material selected from a group of alphahydroxy acids.

14. The cancer treatment method of claim 7 further comprising blending high molecular weight hyaluronic acid with the conjugation.

15. The cancer treatment method of claim 5 with the first cytotoxic agent adapted to damage a cell's ability to accurately replicate, and with the second cytotoxic agent adapted to paralyze a cell's cytoskeleton.

* * * * *